United States Patent [19]

Schumacher et al.

[11] Patent Number: 5,227,494

[45] Date of Patent: Jul. 13, 1993

[54] PROCESS FOR PREPARING OXAZOLINE COMPOUNDS

[75] Inventors: Doris P. Schumacher, Bedminster; Jon E. Clark, Highland Park; Bruce L. Murphy, Glen Ridge, all of N.J.

[73] Assignee: Schering Corporation, Kenilworth, N.J.

[21] Appl. No.: 905,951

[22] Filed: Jun. 29, 1992

Related U.S. Application Data

[63] Continuation-in-part of Ser. No. 656,187, Mar. 5, 1991, abandoned, which is a continuation-in-part of Ser. No. 244,126, Sep. 14, 1988, abandoned.

[51] Int. Cl.$^5$ ............................................. C07D 263/08
[52] U.S. Cl. ..................................... 548/237; 548/239
[58] Field of Search ................... 548/237, 239; 544/88

[56] References Cited

U.S. PATENT DOCUMENTS

| | | | |
|---|---|---|---|
| 2,402,198 | 6/1946 | Loder | 548/237 |
| 2,718,520 | 9/1955 | Slack | 548/237 |
| 2,759,001 | 8/1956 | Moersch et al. | 548/237 |
| 2,786,870 | 3/1957 | Slack . | |
| 2,820,041 | 1/1958 | Heywood | 548/237 |
| 3,813,378 | 5/1974 | Witte et al. | 548/237 |
| 3,979,405 | 9/1976 | Toth et al. | 548/237 |
| 4,216,162 | 8/1980 | Arlt | 548/237 |
| 4,235,892 | 11/1980 | Nagabhushan . | |
| 4,743,700 | 5/1988 | Jommi et al. | 548/237 |

FOREIGN PATENT DOCUMENTS

| | | | |
|---|---|---|---|
| 0130633 | 1/1985 | European Pat. Off. . | |
| 90/02738 | 3/1990 | PCT Int'l Appl. | 548/237 |

OTHER PUBLICATIONS

Witte, et al., "Formation of Cyclic Imidic Esters by Reaction of Nitriles with Amino Alcohols", *Liebigs Ann. Chem.* (1974) pp. 996–1009.

*Primary Examiner*—Donald G. Daus
*Attorney, Agent, or Firm*—Paul A. Thompson; Joseph T. Majka; Edward H. Mazer

[57] ABSTRACT

A novel process for regioselectively preparing oxazoline compounds is disclosed. The process utilizes an amino alcohol, a cyano compound, a base and a dihydric alcohol solvent, a polyhydric alcohol solvent or mixtures thereof.

10 Claims, No Drawings

PROCESS FOR PREPARING OXAZOLINE COMPOUNDS

This application is a continuation-in-part of U.S. Application Ser. No. 07/656,187, filed Mar. 5, 1991 now abandoned, which in turn is the United States national application corresponding to International Application No. PCT/US89/03827, filed Sep. 12, 1989 and designating the United States, which PCT application is in turn a continuation-in-part of U.S. application Ser. No. 07/244,126, filed Sep. 14, 1988, now abandoned, the benefit of which is claimed pursuant to the provisions of 35 U.S.C. §§120, 363 and 365(c).

FIELD OF THE INVENTION

The present invention is directed to a novel process for regioselectively preparing oxazoline compounds. Oxazoline compounds are useful in preparing surface active agents, detergents, waxes, and intermediates for pharmaceutical compounds, such as those disclosed in U.S. Pat. No. 4,743,700.

BACKGROUND OF THE INVENTION

Oxazoline compounds are known, and are disclosed in U.S. Pat. Nos. 4,216,162; 3,813,378; 2,786,870; 2,718,520; and 2,820,041.

Processes for making oxazolines are known, such as described in European Patent Application 130,633, U.S. Pat. No. 4,235,892 and the article *"Formation of Cyclic Imidic Esters by Reaction of Nitriles with Amino Alcohols"* by H. Witte and Wolfgang Seeliger, Liebigs Ann Chem. pp 996-1009, (1974) which utilizes catalytic amounts of certain metal salts. U.S. Pat. No. 2,402,198 describes a process for preparing oxazolines by reacting monoethanolamine with a nitrile in the presence of an alkaline catalyst. U.S. Pat. No. 2,759,001 discloses preparing racemic mixtures of isomeric oxazolines by reacting dichloroacetonitrile with an aminodiol compound. U.S. Pat. No. 3,979,405 discloses preparing 2-oxazolines by reacting an amino alcohol with a nitrile in an anhydrous alcohol such as n-butanol or cyclohexanol. None of these references teach a method for preparing oxazolines employing a dihydric or polyhydric alcohol solvent. It would be desirable to provide a process for preparing oxazoline compounds whose yields, purity and selectivity are as good as or better than methods previously taught. It would also be desirable to provide a process for preparing said oxazoline compounds which requires as few or even fewer steps than methods previously taught. It would also be desirable to provide a process which is as economical, if not more so, than previous methods. Further, where two or more potential structural isomers may be formed, it would be highly desirable to provide a process which is regioselective i.e. produces only one structural isomer.

SUMMARY OF THE INVENTION

The present invention is directed toward a process for preparing oxazoline compounds of the formula:

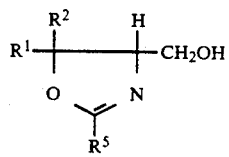

wherein:

$R^1$ and $R^2$ are independently selected from the group consisting of hydrogen, sulfide, sulfoxide, sulfonyl, aryl and substituted aryl; wherein aryl is selected from the group consisting of phenyl, naphthyl, indenyl or indanyl; and wherein substituted groups are substituted by substituents independently selected from the group consisting of halo, alkyl of 1-6 carbons, aryl as defined above, cyano, carboxyl or salts thereof, nitro and hydroxyl; and $R^5$ is selected from the group consisting of hydrogen, alkyl, haloalkyl, cycloalkyl or substituted cycloalkyl, cycloalkalkyl or substituted cycloalkalkyl, alkenyl or substituted alkenyl, alkynyl, alkenylalkyl or substituted alkenylalkyl, alkynylalkyl or substituted alkynylalkyl, alkoxyalkyl or substituted alkoxyalkyl, dialkylaminoalkyl, aryl or substituted aryl, arylalkyl or substituted arylalkyl, arylalkenyl or substituted arylalkenyl, alkoxyaryl or substituted alkoxyaryl, aryloxyaryl or substituted aryloxyaryl, aryloxyalkyl or substituted aryloxyalkyl, acyl or substituted acyl, aromatic heterocyclic or substituted aromatic heterocyclic, heterocyclic alkyl or substituted heterocyclic alkyl, heterocyclic cycloalkyl or substituted heterocyclic cycloalkyl, heterocyclic cycloalkylalkyl or substituted heterocyclic cycloalkylalkyl, sulfoxide or substituted sulfoxide, sulfonyl or substituted sulfonyl, sulfide or substituted sulfide, or hydroxyalkyl; wherein aryl is selected from the group consisting of phenyl, naphthyl, indenyl or indanyl; and wherein substituted groups are substituted by substituents independently selected from the group consisting of halo, alkyl of 1-6 carbons, aryl as defined above, carboxyl or salts thereof, and nitro.

The process comprises the step of regioselectively contacting a cyano compound of the formula

with an aminoalcohol compound of the formula

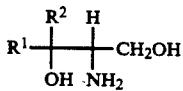

or salt thereof, wherein $R^1$, $R^2$ and $R^5$ are as defined hereinbefore, performed in the presence of a base and an alcohol solvent, wherein said solvent is a dihydric alcohol solvent, a polyhydric alcohol solvent or mixture thereof. Preferably $R^5$ is phenyl, 4-nitrophenyl, cinnamyl, 4-methoxy-cinnamyl or dichloromethyl. More preferably, $R^2$ is 4-methylthiophenyl, 4-methyl-SO-phenyl or 4-methyl-SO$_2$-phenyl; $R^5$ is phenyl, p-nitrophenyl or dichloromethyl; and $R^1$ is hydrogen. Preferably the base is diazabicycloundecene, more specifically 1,8-diazobicyclo[5.4.0]undec-7-ene (DBU) or an alkali metal carbonate, most preferably potassium carbonate. Also, preferred is that the cyano compound and the aminoalcohol compound be contacted in the presence of a polyhydric alcohol, most preferably glycerol, or in a mixture of a dihydric alcohol and a polyhydric alcohol, most preferably a mixture of ethylene glycol and glycerol.

As stated above, the instantly claimed process is regio-selective. That is, although the reaction potentially can give rise to two or more structural isomers, the present process produces only one of the two or more potential structural isomers.

The process has the advantages of being able to prepare an oxazoline compound of formula (X) in high yields, good purity, high specificity, with low by-product formation using relatively mild reaction conditions with as few or fewer steps than other processes previously taught. The present invention has the further advantage of providing a process of preparing oxazoline compounds as economically, if not more so, than other processes previously taught. The present invention has the further advantage of providing a process for preparing oxazoline compounds whose stereoisomeric configuration can be easily determined aforehand simply by the selection of the appropriate starting materials. An especially advantageous feature of the present invention is that it is regioselective and that virtually no racemization occurs when chiral starting material of formula IX are used.

DETAILED DESCRIPTION OF THE EMBODIMENTS

When utilized in the present specification and in the appended claims the terms listed hereinbelow, unless otherwise indicated are defined as follows:

The term "alkyl" refers to a straight saturated hydrocarbon moiety (i.e. hydrocarbons having carbon-carbon single bonds) containing from 1 to 6 carbon atoms, or a branched saturated hydrocarbon moiety of 3 to 6 carbon atoms, such as methyl (i.e. —CH$_3$), ethyl, propyl, isopropyl, butyl, isobutyl, tert-butyl, pentyl or hexyl; the term "substituted alkyl" refers to an alkyl moiety which if further substituted at the carbon by one or more of the following groups: halo, alkyl of one to six carbon atoms, aryl of six to fifteen carbon atoms, cyano (i.e. —CN), carboxyl (i.e. —COOH) or salts thereof, nitro (i.e. —NO$_2$) and hydroxyl;

The terms "halogen" and "halo" refers to fluoride, chloride, bromide or iodide;

The term "haloalkyl" refers to an alkyl moiety in which one or more of the hydrogen atoms has been replaced by a halogen atom, such as chloromethyl, fluoromethyl, bromomethyl, trifluoromethyl, dichloromethyl, 2-chloro-2-fluoroethyl or 6,6,6-trichlorohexyl;

The term "cycloalkyl" refers to a saturated carbocyclic ring characterized by closed rings and containing from 3 to 6 carbon atoms, such as cyclopropyl, cyclobutyl, cyclopentyl or cyclohexyl; the term "substituted cycloalkyl" refers to a cycloalkyl moiety which is further substituted at the carbon by one or more of the following groups: halo, alkyl of one to six carbon atoms, aryl of six to fifteen carbon atoms, cyano, carboxyl, or salts thereof, nitro and hydroxyl;

The term "cycloalkalkyl" refers to a cycloalkyl moiety of 3 to 6 carbon atoms covalently bonded to an alkyl moiety of 1 to 6 carbon atoms; the term substituted "cycloalkalkyl" refers to a cycloalkalkyl moiety which is further substituted at the carbon by one or more of the following groups: halo, alkyl of one to six carbon atoms, aryl of six to fifteen carbon atoms, cyano (i.e. —CN), carboxyl (i.e. —COOH) or salts thereof, nitro (i.e. —NO$_2$) and hydroxyl;

The term "alkenyl" refers to a straight hydrocarbon moiety of two to six carbon atoms or a branched hydrocarbon moiety of three to six carbon atoms having at least one carbon-carbon double bond, such as ethenyl (i.e. —CH=CH$_2$), propenyl, 1-butenyl, 2-butenyl, isobutenyl, 1-pentenyl, 2-methyl-1-butenyl or 1-hexenyl; the term "substituted alkenyl" refers to an alkenyl moiety which is further substituted at a substitutable carbon by one or more of the following groups: halo, alkyl of one to six carbon atoms, aryl of six to fifteen carbon atoms, cyano, carboxyl or salts thereof, nitro and hydroxyl;

The term "alkynyl" refers to a straight hydrocarbon moiety of two to six carbon atoms or a branched hydrocarbon moiety of four to six carbon atoms having one carbon to carbon triple bond such as ethynyl (i.e. —C≡CH), 1-propynyl, 1-butynyl, 1-pentynyl, 2-pentynyl, 1-hexynyl, 2-hexynyl or 3-hexynyl; the term "substituted alkynyl" refers to an alkynyl moiety which is further substituted at a substitutable carbon by one or more of the following groups: halo, alkyl of on to six carbon atoms, aryl of six to fifteen carbon atoms, cyano, carboxyl or salts thereof, nitro and hydroxyl;

The term "alkoxy" refers to an alkyl moiety containing from 1 to 6 carbon atoms covalently bonded to an adjacent structural element through an oxygen atom, such as methoxy (i.e. —OCH$_3$), ethoxy, propoxy, isopropoxy, butoxy, pentoxy or hexoxy; the term "substituted alkoxy" refers to an alkoxy moiety which is further substituted at the carbon by one or more of the following groups: halo, alkyl of one to six carbon atoms, aryl of six to fifteen carbon atoms, cyano, carboxyl or salts thereof, nitro and hydroxyl;

The term "alkenylalkyl" refers to an alkenyl moiety of two to six carbon atoms covalently bonded to a alkyl moiety of 1 to 6 carbon atoms; the term "substituted alkenylalkyl" refers to an alkenylalkyl moiety which is further substituted at a carbon by one or more of the following groups: halo, alkyl of one to six carbon atoms, aryl of six to fifteen carbon atoms, cyano, carboxyl or salts thereof, nitro and hydroxyl;

The term "alkynylalkyl" refers to an alkynyl moiety of two to six carbon atoms covalently bonded to an alkyl moiety of 1 to 6 carbon atoms; the term "substituted alkynylalkyl" refers to an alkynylalkyl moiety which is further substituted at the carbon by one or more of the following groups: halo, alkyl of one to six carbon atoms, aryl of six to fifteen carbon atoms, cyano, carboxyl or salts thereof, nitro and hydroxyl;

The term "alkoxyalkyl" refers to an alkoxy moiety of 1 to 6 carbon atoms covalently bonded to an alkyl moiety of 1 to 6 carbon atoms; the term "substituted alkoxyalkyl" refers to an alkoxyalkyl moiety which is further substituted at a carbon by one or more of the following groups: halo, alkyl of one to six carbon atoms, aryl of six to fifteen carbon atoms, cyano, carboxyl or salts thereof, nitro and hydroxyl;

The term "amino" refers to a primary (—NH$_2$), a secondary or a tertiary amine wherein each hydrogen can be substituted by an alkyl moiety of one to six carbon atoms or by an aryl moiety of six to fifteen carbon atoms;

The term "dialkylaminoalkyl" refers to a nitrogen atom covalently bonded to three alkyl moieties having 1 to 6 carbon atoms in each alkyl moiety, and one alkyl moiety is bonded to an adjacent structural element.

The term "aryl" refers to a carbocyclic moiety containing at least one benzenoid-type ring, with the aryl groups preferably containing from 6 to 15 carbon atoms, for example, phenyl, naphthyl, indenyl or indanyl; the term "substituted aryl" refers to an aryl moiety which is further substituted at the carbon by one or more of the following groups: halo, alkyl of one to six carbon atoms, aryl of six to fifteen carbon atoms, cyano, carboxyl or salts thereof, nitro and hydroxyl;

The term "arylalkyl" refers to an aryl moiety of 6 to 15 carbon atoms covalently bonded to an alkyl moiety of one to six carbon atoms such as benzyl or phenylethyl; the term "substituted aralkyl" refers to an aralkyl moiety which is further substituted at the carbon by one or more of the following groups: halo, alkyl of one to six carbon atoms, aryl of six to fifteen carbon atoms, cyano, carboxyl or salts thereof, nitro and hydroxyl;

The term "arylalkenyl" refers to an aryl moiety of six to fifteen carbon atoms covalently bonded to an alkenyl moiety of two to six carbon atoms, such as 2-phenyl-1-ethenyl (cinnamyl) or 4-phenyl-2-butenyl; the term "substituted arylalkenyl" refers to an arylalkenyl moiety which is further substituted at the carbon by one or more of the following groups: halo, alkyl of one to six carbon atoms, aryl of six to fifteen carbon atoms, cyano, carboxyl or salts thereof, nitro and hydroxyl;

The term "arylalkoxy" refers to an aryl moiety of one to six carbon atoms covalently bonded to an alkoxy moiety of one to six carbon atoms; the term "substituted arylalkoxy" refers to an arylalkoxy moiety which is further substituted at the carbon by one or more of the following groups: halo, alkyl of one to six carbon atoms, aryl of six to fifteen carbon atoms, cyano, carboxyl or salts thereof, nitro and hydroxyl;

The term "aryloxy" refers to an aryl moiety covalently bonded through an oxygen (i.e. —O—) atom, such as phenoxy; the term "substituted aryloxy" refers to an aryloxy moiety which is further substituted at the carbon by one or more of the following groups: halo, alkyl of one to six carbon atoms, aryl of six to fifteen carbon atoms, cyano, carboxyl or salts thereof, nitro and hydroxyl;

The term "alkoxyaryl" refers to an alkoxy moiety of one to six carbon atoms covalently bonded to an aryl moiety of six to 15 carbon atoms, such as 2-methoxyphenyl, 2-or 4-ethoxynaphthyl or 6-propoxyindenyl; the term "substituted alkoxyaryl" refers to an alkoxyaryl moiety which is further substituted at the carbon by one or more of the following groups: halo, alkyl of one to six carbon atoms, aryl of six to fifteen carbon atoms, cyano, carboxyl, or salts thereof, nitro and hydroxyl;

The term "aryloxyaryl" refers to an aryloxy moiety as defined hereinbefore covalently bonded to an aryl moiety of six to 15 carbon atoms, such as phenoxyphenyl or 1-naphthyloxyphenyl; the term "substituted aryloxyaryl" refers to an aryloxyaryl moiety which is further substituted at the carbon by one or more of the following groups: halo, alkyl of one to six carbon atoms, aryl of six to fifteen carbon atoms, cyano, carboxyl or salts thereof, nitro and hydroxyl;

The term "aryloxyalkyl" refers to an aryloxy moiety as defined hereinbefore covalently bonded to an alkyl moiety of one to six carbon atoms, such as phenoxymethyl or 1-naphthyloxyethyl; the term "substituted aralkyl" refers to an aralkyl moiety which is further substituted at the carbon by one or more of the following groups: halo, alkyl of one to six carbon atoms, aryl of six to fifteen carbon atoms, cyano, carboxyl or salts thereof, nitro and hydroxyl;

The term "acyl" refers to a carbonyl moiety

bonded to a hydrogen, alkyl, aryl, alkoxy, amino or an aryloxy group such as a formyl moiety

, an alkanoyl moiety

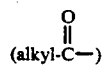

of one to six carbon atoms in the alkyl portion, an aroyl moiety

of six to 15 carbon atoms in the aryl portion, an ester moiety

of one to six carbon atoms in the alkoxy portion, an amide moiety

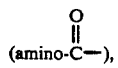, or an aryloxy moiety. Typical acyl groups include acetyl, benzoyl and ethoxycarbonyl; the term "substituted acyl" refers to the alkyl, aryl, alkoxy, amino, aryloxy, alkanoyl, aroyl, ester, amide or aryloxy portion of the acyl moiety which is further substituted at a carbon by one or more of the following groups: halo, alkyl of one to six carbon atoms, aryl of six to fifteen carbon atoms, cyano, carboxyl or salts thereof, nitro and hydroxyl;

The term "aromatic heterocyclic" refers to a cyclic moiety having at least one O, S and/or N hetero-atom interrupting the ring structure and having a sufficient number of unsaturated carbon to carbon double bonds and/or nitrogen to carbon double bonds, to provide aromatic character, with the aromatic heterocyclic groups preferably containing from 2 to 14 carbon atoms, for example, 2-, 3-or 4-pyridyl, 2- or 3-furyl, 2- or 3-thienyl, 2-, 4- or 5-thiazolyl, 2-, 4- or 5-imidazolyl, 2-, 4- or 5-pyrimidinyl, 2-pyrazinyl, 3- or 4-pyridazinyl, 3-, 5- or -6-[1,2,4-triazinyl], 3- or 5-[1,2,4-thiadiazolyl], 2-, 3-, 4-, 5-, 6- or 7-benzofuranyl, 2-, 3-, 4-, 5-, 6- or 7-indolyl, 3-, 4- or 5-pyrazolyl, 2-, 4- or 5-oxazolyl; the term "substituted aromatic heterocyclic" refers to an aromatic heterocyclic moiety which is further substituted at a carbon or heteroatom by one or more of the following groups: halo, alkyl of one to six carbon atoms, aryl of six to fifteen carbon atoms, cyano, carboxyl or salts thereof, nitro and hydroxyl;

The term "heterocyclic alkyl" refers to an aromatic heterocyclic moiety of 2 to 14 carbon atoms as defined hereinbefore, covalently bonded to an alkyl moiety of one to six carbon atoms; the term "substituted heterocyclic alkyl" refers to a heterocyclic alkyl moiety which is further substituted at a carbon or heteroatom by one or more of the following groups: halo, alkyl of one to six carbon atoms, aryl of six to fifteen carbon atoms, cyano or salts thereof, nitro and hydroxyl;

The term "heterocyclic cycloalkyl" refers to a saturated carbocyclic ring of two to six carbon atoms having at least one oxygen, sulfur or nitrogen atom, or combination thereof, interrupting the ring structure, and are substituted at a carbon atom, such as 2-, 3-, or 4-piperidyl, 2-dioxanyl, 2- or 3-oxazetidinyl, 2-oxiranyl or 3-, 4-, 5- or 6-thiazinyl; the term "substituted heterocyclic cycloalkyl" refers to an heterocyclic cycloalkyl moiety which is further substituted at the carbon by one or more of the following groups: halo, alkyl of one to six carbon atoms, aryl of six to fifteen carbon atoms, cyano, carboxyl or salts thereof, nitro and hydroxyl;

The term "heterocyclic cycloalkylalkyl" refers to a heterocyclic cycloalkyl moiety of two to six carbon atoms covalently bonded to an alkyl moiety of one to six carbon atoms; the term "substituted cycloalkalkyl" refers to a cycloalkalkyl moiety which is further substituted at the carbon by one or more of the following groups: halo, alkyl of one to six carbon atoms, aryl of six to fifteen carbon atoms, cyano, carboxyl or salts thereof, nitro and hydroxyl;

The term "sulfoxide" refers to a sulfoxide moiety (i.e. R—SO—R—) wherein each R independently represents an alkyl moiety of one to six carbon atoms or an aryl moiety of 6 to 15 carbon atoms, such as

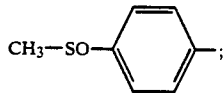

the term "substituted sulfoxide" refers to a sulfoxide moiety as defined above where "R" group is further substituted at the carbon by one or more of the following groups: halo, alkyl of one to six carbon atoms, aryl of six to fifteen carbon atoms, cyano, carboxyl or salts thereof, nitro and hydroxyl;

The term "sulfonyl" refers to a sulfonyl moiety (i.e. R—SO$_2$—R—) salts wherein each R independently represents alkyl of one to six carbon atoms or aryl of six to twelve carbon atoms, such as

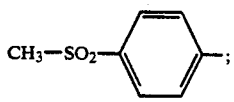

the term "substituted sulfonyl" refers to a sulfonyl moiety as defined above whose "R" group is further substituted at the carbon by one or more of the following groups: halo, alkyl of one to six carbon atoms, aryl of six to fifteen carbon atoms, cyano, carboxyl or salts thereof, nitro and hydroxyl;

The term "sulfide" refers to a sulfide moiety (i.e. R—S—R—) wherein each R independently represents alkyl of one to six carbon atoms or aryl of six to twelve carbon atoms, such as alkylthioalkyl, or alkylthioaryl such as

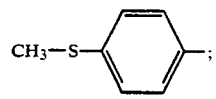

the term "substituted sulfide" refers to a sulfide moiety as defined above whose "R" group is further substituted at the carbon by one or more of the following groups: halo, alkyl of one to six carbon atoms, aryl of six to fifteen carbon atoms, cyano, carboxyl or salts thereof, nitro and hydroxyl;

The term "hydroxyalkyl" refers to an alkyl moiety in which one or more of the hydrogens is replaced by a hydroxy moiety, such as hydroxymethyl (i.e. -CH$_2$OH), hydroxyethyl, 1-hydroxypropyl, 2-hydroxypropyl, 3-hydroxybutyl or 4-hydroxyhexyl.

The base employed in the present process is any substance which will remove a proton from the hydroxyl (—OH) of the moiety

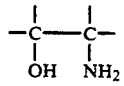

in order to cyclize the amino alcohol (IX) with the cyano compound (VIII) to give the desired oxazoline compound (X). The base is neither the amino alcohol (IX) nor the cyano compound (VIII).

Bases which can be employed in process of the present invention can be a non-aqueous base such as lithium diisopropyl amide, lithium hexamethylsilazide, sodium hexamethylsilazide and potassium hexamethylsilazide; or potassium t-butoxide and. sodium methoxide. The base can be an alkali metal carbonate such as sodium, potassium, lithium or cesium carbonate or an alkaline earth metal carbonate such as calcium or barium carbonate; hydroxides such as sodium and potassium hydroxides; and hydrides such as sodium or potassium hydrides. The base can also be ammonia (NH$_3$) or an organic base including urea; a secondary amine such as dimethylamine, diphenylamine, N-methyl N-propylamine, diethylamine, diisopropylamine, N-methylaniline, piperazine, piperidine, pyrrolidine; or a tertiary amine such as trimethylamine, dimethylaniline, N,N-dimethylpropylamine, N,N-dimethylpiperidine, N,N-dimethylbutylamine, triethylamine. The base can also be an heterocyclic nitrogen containing compound such as isoquinoline, morpholine, purine, pyridine, pyrazine, pyrimidine, quinoline or polyvinyl pyridine, preferably DBU. Other bases which may be suitably employed in the present process are disclosed in "Modern Synthetic Reactions" by H. House, W. A. Benjamin, Inc., Menlo Park, Calif., 1972, 856 pages. Where appropriate, mixtures of any of the above bases can be employed.

The base is used in amounts effective to remove the requisite proton from the hydroxy moiety. Such amounts in terms of mole ratios (moles base:mole amino alcohol (IX)) can range from about 1,000 to 0.001:1, preferably from about 10 to 0.01:1, more preferably from about 1 to 0.1:1, most preferably about 0.15:1.

The alcohol solvent employed in the present invention is preferably dihydric (two OH groups-diols) such as C-2 to C-10 glycols and derivatives. Representative C-2 to C-10 glycols and derivatives include ethylene glycol, propylene glycol, 1,2-butanediol, 1,4- butanediol, pentanediols and the like, more preferably ethylene glycol.

The alcohol solvent employed in the present invention is also preferably polyhydric (three or more OH groups-polyols). Representative polyhydric alcohols include glycerol (1,2,3-propanetriol), 1,2,4-butanetriol, pentaerythritol and the like, more preferably glycerol. Where suitable, the process of the present invention can employ a mixture of a dihydric and a polyhydric alcohol, most preferably ethylene glycol and glycerol in a volume ratio of 2:1 (ethylene glycol:glycerol).

The alcohol solvent employed in the present process can be used in amounts which can range from an amount sufficient to at least partially solubilize one or both of the reactants and/or the desired product to an amount in excess of either starting reactant. Generally the amount of alcohol solvent can range from about 1 to 5,000 percent or more by weight of an individual reactant, preferably from about 100 to 1,000 percent by weight, most preferably from about 100 to about 300 percent.

In the process of preparing the oxazoline compound of formula (X), the cyano compound (VIII) is contacted with the aminoalcohol (IX) in amounts and under conditions effective to yield the desired oxazoline compound of formula (X). The cyano compound (VIII) is contacted with the aminoalcohol (IX) at temperatures ranging from about −10 to about 200 degrees Centigrade (°C.), preferably from about 70° to about 150° C., most preferably from about 100° to about 110° C. The contacting is performed at ambient pressures although pressures greater or less than ambient can be employed. The contacting of the reactants can be carried out for about 5 minutes to about 72 hours or more until the reaction is substantially completed, preferably from about 1 hour (hr) to about 48 hours. Also preferred is that the reactants are stirred during the contacting procedures. The cyano compound (VIII) can be contacted with the amino alcohol of (IX) in molar ratios ranging from about 100 to 0.1:1; (moles cyano compound (VIII):mole amino alcohol (IX)), preferably from about 10 to 1:1, most preferably from about 2 to 1:1.

The stereochemistry of the oxazoline compounds (X) is preserved with respect to the stereochemistry of the starting materials. For example, when an amino alcohol of S,S' configuration is contacted with benzonitrile, the resultant oxazoline (X) has a S,S' stereoisomeric configuration.

After the reaction is completed, the desired oxazoline compound (X) can be recovered by conventional separatory and recovery methods such as phase separation, distillation or evaporation of any solvents present, crystallization, chromatography, filtration and the like. For example, the reaction mixture can be diluted with water and the oxazoline compound (X) is recovered by filtration.

PREPARATION OF STARTING MATERIALS

The cyano compounds (VIII) are known and can be prepared by conventional procedures, such as for example, by dehydration of the corresponding amide with a dehydrating agent such as phosphorous oxychloride. The dehydration reaction is illustrated as follows:

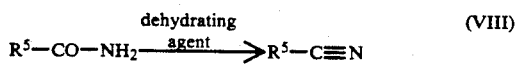

(VIII)

wherein $R^5$ is as defined hereinbefore. Similarly, other methods for preparing the cyano compounds (VIII) are disclosed in references such as H. O. House, Modern Synthetic Reactions, Second Edition, W. A. Benjamin Inc., (1979) pp. 79 and 623-628, whose preparation teachings are incorporated herein by reference.

The aminoalcohol compounds (IX) are known and can be prepared by conventional procedures, such as, for example by epoxidation of the corresponding olefin (V) by an epoxidizing method, followed by cleavage of the epoxide ring (VI) by azide to give the azido compound (VII), followed by reduction of the azido compound with a reducing agent to give the requisite aminoalcohol (IX). The procedure can be illustrated as follows:

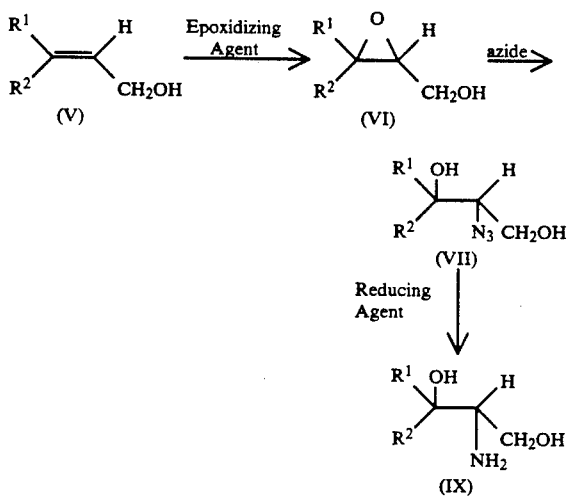

wherein $R^1$ and $R^2$ are as defined hereinbefore. Representative epoxidizing methods include any suitable peracid reactant such as, for example, pertrifluoro-acetic acid

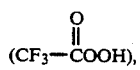

perbenzoic acid

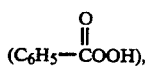

peracetic acid

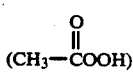

and the like, as well as formation of a halohydrin followed by base.

In situations where any of $R^1$ or $R^2$ of olefin compound (V) contains an oxidizable functionality, such as an unsaturated bond, the olefin compound (V) can be selectively epoxidized and/or the requisite epoxide ring compound (VI) thus prepared can be further isolated in order to prepare the azido compound (VII). Representative azides include those of alkali earth metals, such as sodium azide, potassium azide, lithium azide, and the like.

The term "reducing agent" refers to any substance which will furnish electrons by its capacity to lose electrons easily, in order to cause the azido compound (VII) receiving the electrons to be reduced to the desired amino alcohol (IX). Examples of reducing agents include, but are not limited to hydrogenating agents and to metal hydrides, such as lithium aluminum hydride (LiAlH$_4$).

The term "hydrogenating agent" is intended to include the requisite hydrogenating catalyst(s) and hydrogen (H$_2$) source for reducing the azido compound (VII) to the aminoalcohol (IX). Various selected catalysts and conditions are described in "Catalytic Hydrogenation in Organic Synthesis", (1978) Morris Freifelder, Chapter 4, Olefins, pg. 15-25, John Wiley and Sons. For example, the hydrogenating catalyst can be nickel, palladium, platinum, platinum oxide, platinum on carbon, and mixture thereof.

Similarly, in situations where R$^1$ or R$^2$ of azido compound (VII) contains a reducible functionality such as an unsaturated bond or a sulfur atom, azido compound (VII) can be reduced with a selective reducing agent and/or the requisite amino alcohol (IX) thus prepared can be further isolated in order to prepare oxazoline compound (X).

Other representative methods of preparing the aminoalcohols of formula (IX) are described in Leroy G. Wade, Jr., Vol. 5, John Wiley and Sons, (1984) pp. 430-431 and in Calvin Buchler and Donald Pearson, *Survey of Organic Synthesis*, Vol. 1, Wiley Interscience, N. Y. (1970), pp. 226, 466 and 475. The preparative teachings of these references are incorporated herein by reference.

Salts of the aminoalcohol (IX) can be prepared by contacting the aminoalcohol (IX) with organic or inorganic acids. Representative organic acids include but are not limited to oxalic, tartaric, acetic, trifluoroacetic, citric, maleic and the like. Representative inorganic acids include hydrochloric, sulfuric or phosphoric acids in about equimolar amounts or in amounts less than equimolar of the acid relative to the aminoalcohol.

The following examples illustrate the present invention in a manner of which it can be practiced but, as such, should not be construed as limitations upon the overall scope of the same.

EXAMPLE 1

PREPARATION OF D-4-HYDROXYMETHYL-5-[4-(METHYLMERCAPTO)PHENYL]-2-PHENYL-2-OXAZOLINE

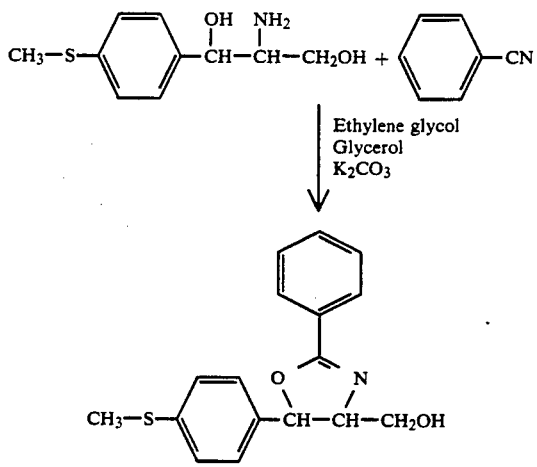

A suspension of 5 grams (g) (23.5 millimole (mmole)) of D(—)-2-amino-1-(4-methylmercaptophenyl)-1,3-propanediol (available from Fuji Chemical Co., Japan) and 0.5 g (3.6 mmole) of potassium carbonate (K$_2$CO$_3$) in 7.5 milliliters (mL) of ethylene glycol and 4.1 mL of glycerol is heated to a temperature of 105° C. with stirring. Benzonitrile (4 mL, 39.2 mmole, 1.67 equivalents) is added and the mixture is stirred at 105° C. for 18 hr under a blanket of nitrogen gas. Completeness of reaction is determined by thin layer chromatography (TLC) on silica gel (9:1-methylene chloride: methanol). The product is isolated by precipitation into water, to give 6.8 g (purity 97%, 22.0 mmole) a 93 percent yield.

EXAMPLE 2

PREPARATION OF D-4-HYDROXYMETHYL-5-[4-(METHYLMERCAPTO)PHENYL]-2-(4-NITROPHENYL)-2-OXAZOLINE

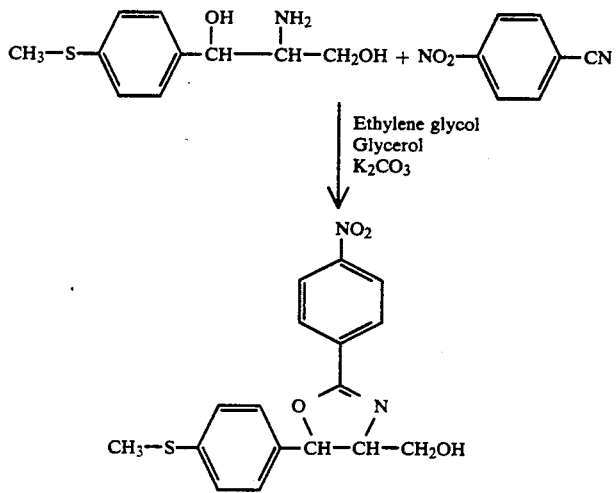

To a mixture of 1 g of D(—)-2-amino-1-(4-methylmercaptophenyl)-1,3-propanediol (4.7 mmole) and 0.1 g of potassium carbonate in 1.5 mL of ethylene glycol and 0.8 mL of glycerol, heated to a temperature of 100° C., 1.0 g of p-nitrobenzonitrile is added, and stirred for 3 hours. Analysis of the reaction mixture by high pressure liquid chromatography indicates a yield of title compound to be 85 percent.

EXAMPLE 3

PREPARATION OF D-(−)-threo-4-HYDROXYMETHYL-5-[4-(METHYLSULFONYL)PHENYL]-2-PHENYL-2-OXAZOLINE

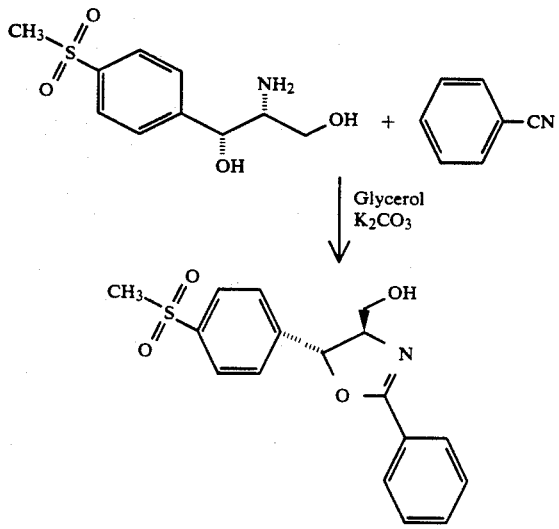

To a mixture of 5 g of D-(−)-threo-2-amino-1-(4-(methylsulfonyl)phenyl)-1,3-propanediol (20.4 mmole), 10 mL of glycerol and 0.43 g of potassium carbonate (3.1 mmole), heated to a temperature of 115° C., add 3.5 g of benzonitrile (33.9 mmole) and stir for 18 hours at 115° C. Cool the mixture and pour into 100 mL of cold water to precipitate the product. Filter to collect the solid product, and wash the solid with cold water and methylene chloride. Dry the product under vacuum to give 6.4 g (97% pure) of the title compound, m.p. 206°-209° C., $[\alpha]_D^{26} = 116.4°$ (DMF).

Using the starting compounds, substantially the same procedure as described in Example 3, and the indicated base and solvent, the results summarized in the following table were obtained for the formation of D-(−)-threo-4-hydroxymethyl-5-[4-(methylsulfonyl)phenyl]-2-phenyl-2-oxazoline.

| Solvent | Ratio[1] | Temp. | Base | Yield[2] | regio-isomer* |
|---|---|---|---|---|---|
| methanol | 5:1 | 100° C. | DBU† | 81% | 11% |
| n-butanol | 5:1 | 120° C. | DBU | 83% | 11% |
| ethylene glycol | 5:1 | 165° C. | DBU | 84% | 1% |
| ethylene glycol | 3:1 | 90° C. | K₂CO₃ | 90% | 1% |
| glycerol | 3:1 | 95° C. | K₂CO₃ | 86% | 0.5% |
| 1,4-butenediol | 3:1 | 95° C. | K₂CO₃ | 81% | 2.9% |
| 1,2-butanediol | 3:1 | 95° C. | K₂CO₃ | 54% | 9.4% |
| 1,4-butanediol | 3:1 | 95° C. | K₂CO₃ | 48% | 11% |
| 1,3-propanediol | 3:1 | 95° C. | K₂CO₃ | 9% | 11% |
| ethylene glycol & glycerol (1:1) | 3:1 | 95° C. | K₂CO₃ | 94% | 9.5% |

[1]ratio of solvent to aminoalcohol (mL/g).
[2]Isolated yield of the desired product.
*Percentage of regio-isomeric oxazoline formed.
† DBU = 1,8-diazobicyclo[5.4.0]undec-7-ene While the present invention has been described in conjunction with the specific embodiments set forth above, many alternatives, modifications, and variations thereof will be apparent to those of ordinary skill in the art. All such alternatives, modifications and variations are intended to fall within the spirit and scope of the present invention.

What is claimed is:

1. A process for preparing an oxazoline compound of the formula:

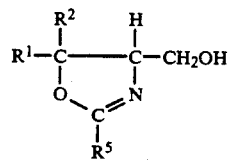

wherein:
  R[1] and R[2] are independently selected from the group consisting of hydrogen, sulfide, sulfoxide, sulfonyl, aryl and substituted aryl; wherein aryl is selected from the group consisting of phenyl, naphthyl, indenyl or indanyl; and wherein substituted groups are substituted by one substituent independently selected from the group consisting of halo, alkyl of 1-6 carbons, aryl as defined above, cyano, carboxyl or salts thereof, nitro and hydroxyl; and
  R[5] is selected from the group consisting of hydrogen, alkyl, haloalkyl, cycloalkyl or substituted cycloalkyl, cycloalkalkyl or substituted cycloalkalkyl, alkenyl or substututed alkenyl, alkynyl, alkenylalkyl or substituted alkenylalkyl, alkynylalkyl or substituted alkynylalkyl, alkoxyalkyl or substituted alkoxyalkyl, dialkylaminoalkyl, aryl or substituted aryl, arylalkyl or substituted arylalkyl, arylalkenyl or substituted arylalkenyl, alkoxyaryl or substituted alkoxyaryl, aryloxyaryl or substituted aryloxyaryl, aryloxyalkyl or substituted aryloxyaryl, acyl or substituted acyl, aromatic heterocyclic or substituted aromatic heterocyclic, heterocyclic alkyl or substituted heterocyclic alkyl, heterocyclic cycloalkyl or substituted heterocyclic cycloalkyl, heterocyclic cycloalkylalkyl or substituted heterocyclic cycloalkylalkyl, sulfoxide or substituted sulfoxide, sulfonyl or substituted sulfonyl, sulfide or substituted sulfide, or hydroxyalkyl; wherein aryl is selected from the group consisting of phenyl, naphthyl, indenyl or indanyl; and wherein substituted groups are substituted by one substituent independently selected from the group consisting of halo, alkyl of 1-6 carbons, aryl as defined above, carboxyl or salts thereof, and nitro;

comprising regioselectively contacting a cyano compound of the formula

wherein R[5] is as defined above, with an amino alcohol compound of the formula

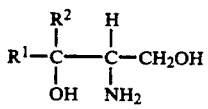

wherein $R^1$ and $R^2$ are as defined above, or a salt thereof in the presence of a base and an alcohol solvent, wherein the solvent is glycerol or a mixture of dihydric and polyhydric alcohols.

2. The process of claim 1 wherein $R^1$ and $R^2$ independently represent hydrogen,

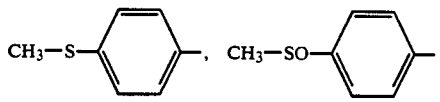

or

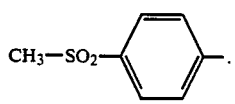

3. The process of claim 1 wherein $R^5$ is phenyl, 4-nitrophenyl, cinnamyl, 4-methoxycinnamyl or dichloromethyl.

4. The process of claim 1 wherein the base is diazabicycloundecene or potassium carbonate.

5. The process of claim 1 wherein the base is employed in an amount ranging from about 10 to 0.01 moles base to one mole amino alcohol.

6. The process of claim 1 wherein the dihydric alcohol solvent is ethylene glycol.

7. The process of claim 1 wherein the polyhydric alcohol solvent is glycerol.

8. The process of claim 1 wherein the cyano compound and the amino alcohol compound are contacted in the presence of a mixture of ethylene glycol and glycerol.

9. The process of claim 1 wherein the contacting is performed at temperatures ranging from about 70° to about 150° C.

10. The process of claim 9 wherein the contacting is performed at temperatures ranging from about 100° to about 110° C.

* * * * *